United States Patent [19]

Kissinger

[11] Patent Number: 4,847,433
[45] Date of Patent: Jul. 11, 1989

[54] PROCESS FOR PREPARING BISPHENOL-A

[75] Inventor: Gaylord M. Kissinger, Evansville, Ind.

[73] Assignee: General Electric Company, Mt. Vernon, Ind.

[21] Appl. No.: 197,182

[22] Filed: May 23, 1988

[51] Int. Cl.$^4$ .............................................. C07C 39/16
[52] U.S. Cl. .................................... 568/727; 568/749
[58] Field of Search ................ 568/727, 763, 724, 749

[56] References Cited

U.S. PATENT DOCUMENTS

| | | | |
|---|---|---|---|
| 4,107,218 | 8/1978 | Konard et al. | 568/724 |
| 4,191,843 | 3/1980 | Kwantes et al. | 568/728 |
| 4,308,405 | 12/1981 | Kwantes et al. | 568/727 |
| 4,348,542 | 9/1982 | Serini et al. | 568/727 |
| 4,375,567 | 3/1983 | Faler | 568/727 |
| 4,766,254 | 8/1988 | Faler et al. | |

Primary Examiner—Werren B. Lone
Attorney, Agent, or Firm—Martin Barancik

[57] ABSTRACT

A process which comprises
(a) contacting an excess of a phenol with a ketone in the presence of an acidic ion exchange resin catalyst;
(b) recovering thereafter a stream from the acidic ion exchange resin catalyst including the dihydric phenol, unreacted phenol, isomers of the desired dihydric phenol and acid impurities derived from the acidic ion exchange resin catalyst;
(c) removing a major portion of the desired dihydric phenol from the stream of (b);
(d) separating the stream including phenol, a small portion of the desired dihydric phenol, isomers of the desired dihydric phenol, and acidic impurities derived from the acidic ion exchange resin catalyst into a major stream and a minor stream by volume;
(e) recycling the major stream so as to contact the acidic ion exchange resin catalyst of (a) together with new phenol and ketone so as to maintain a balance between the color of the final desired dihydric phenol product and impurities found therein;
(f) recovering from the small stream desireable dihydric phenol, and
(g) introducing into the minor stream created at step (d) sufficient quantities of a Group II a metal or transition metal of oxidation number +2 carbonate to effectively neutralize the acidic impurities derived from the acidic ion exchange resin catalyst.

8 Claims, No Drawings

4,847,433

PROCESS FOR PREPARING BISPHENOL-A

BACKGROUND OF THE INVENTION

The dihydric phenols have achieved significant success in their commercial applications. Dihydric phenols are useful in the commercial manufacture of various polymers including the polyarylates, polyamides, epoxies, polyetherimides, polysulfones and the polycarbonates. Significant attention has been directed to the commercial preparations of the dihydric phenols. For many years it has been well known that the acid catalyzed reaction of phenol with specific aldehyde or ketone could prepare the 4,4'-dihydric phenol with specific groups derived from the aldehyde or the ketone connecting the two phenolic rings. In particular when phenol is reacted with acetone, the dihydric phenol 4,4'(hydroxyphenyl)propane-2, hereafter known as bisphenol-A is formed. This has particular utility in polycarbonates, polyarylates and copolyestercarbonates as well as epoxies. In order to make certain polymers, in particular the polycarbonates, the bisphenol-A must be particularly pure, for example, as measured by color. Additionally, the process should be particularly efficient since the dihydric phenol costs contribute substantially to the cost of the final polymer. Therefore much attention has been directed to the recovery of bisphenol-A after preparation. Not only is recovery from the major stream containing primarily bisphenol-A important, but because of the economics involved, various side streams or "purge streams" also containing significant quantities of bisphenol-A should also be investigated for improved recovery techniques.

Various catalytic systems for acid catalysis of the reaction between phenol and bisphenol-A have been investigated and used commercially. At one time the hydrochloric acid catalyzed process was used in a significant number of commercial facilities. However the corrosion caused by the hydrochloric acid on standard metallic reactors and pre and post reaction equipment left much to be desired as far as replacement economics was concerned. Recently, substantial attention has been placed on using an ion exchange resin catalyst system since it does not have a significant acid corrosion problem. However it has recently been discovered in our equipment that the usual processing techniques for recovery of bisphenol-A from recovery streams having relatively small amounts of bisphenol-A, about 6 to 15 weight percent of the process stream, after preparation with the ion exchange catalyst cannot be practiced in the same manner as when using the hydrochloric acid catalyst system. Substantial quantities of bisphenol-A which could be isolated from streams having a major quantity of phenol after reaction with an HCl catalyzed system could no longer be recovered when using an ion exchange system. Additionally the quality of the bisphenol-A which could be recovered as well as the quality of other materials in these "purge streams" was sufficiently lessened as measured by the color of the materials. Color is a very important property of the final polymers which are prepared from the bisphenol-A as well as the bisphenol-A itself. For example, bisphenol-A polycarbonate is known to be clear and colorless.

It has now been discovered that bisphenol-A can be successfully recovered in substantial quantities from the purge streams of an ion exchange catalyzed reaction of a phenol with a ketone, particularly phenol per se with acetone, by utilizing a relatively simple treatment with a specific basic system. Not only is the dihydric phenol recoverable from the purge streams, but the color of the dihydric phenol and the recyclable components is substantially improved.

SUMMARY OF THE INVENTION

In accordance with the invention, there is a process which comprises (a) contacting an excess of a phenol with a ketone in the presence of an acidic ion exchange resin catalyst;

(b) recovering thereafter a stream from an acidic ion exchange resin catalyst, said stream including the dihydric phenol, unreacted phenol, isomers of the desired dihydric phenol and acid impurities derived from the acidic ion exchange resin catalyst;

(c) removing a major portion of the desired dihydric phenol from the stream of (b);

(d) separating the stream including phenol, a small portion of the desired dihydric phenol, isomers of the desired dihydric phenol, and acidic impurities derived from the acidic ion exchange resin catalyst into a major stream and a minor stream by volume;

(e) recycling the major stream so as to contact the acidic ion exchange resin catalyst of (a) together with new phenol and ketone so as to maintain a balance between the color of the final desired dihydric phenol product and impurities found therein;

(f) recovering from the small stream desirable dihydric phenol, and (g) introducing into the minor stream created at step (d) sufficient quantities of a Group II-a metal or transition metal of oxidation number +2 carbonate to effectively neutralize the acidic impurities derived from the acidic ion exchange resin catalyst.

In further accordance with the invention there is a process for preparing and isolating a dihydric phenol from the reaction of a phenol and a ketone in the presence of an acidic ion exchange resin catalyst, the improvement comprising the addition to the process of sufficient quantities of a Group II-a metal or transition metal of oxidation number +2 carbonate to a minor portion of the split process stream created after the removal from the stream of a major quantity of the desired dihydric phenol to effectively neutralize acidic impurities provided from the acidic ion exchange resin catalyst, said impurities carried with the desired dihydric phenol in the downstream processing steps from the catalyst.

DETAILED DESCRIPTION OF THE INVENTION

The most well known dihydric phenol is bisphenol-A. The invention shall be further described in detail with the production of bisphenol-A. However, any other dihydric phenol is anticipated to have these problems if made from the reaction of a phenol with an acetone and an acidic ion exchange resin catalyst system which has produced acidic impurities.

Phenol and acetone are passed into a reactor having an acidic ion exchange resin catalyst system. Such catalyst system is usually an Amberlite type resin obtained from Rohm and Haas. This resin has a styrenic backbone with pendant $SO_3H$ groups which provide the acidic character to the resin. Usually the styrene is crosslinked with a small quantity of divinyl benzene or other crosslinking chemical. This addition of a crosslinker appears to provide structural strength and rigidity to the catalyst. The phenol in excess, together with the acetone, is passed over the acidic ion exchange resin. Other ion exchange resins can also be used although it is preferable to use the styrenic backbone crosslinked with the difunctional monomer and having $SO_3H$ groups pendant from the aromatic nucleus of the styrene moiety.

The stream coming off the catalyst has the bisphenol-A, excess phenol, isomers of bisphenol-A, isopropenyl phenol (IPP), chromans (which are addition products of various bisphenols), spiro biindanes and other side reaction products of the reaction of the phenol with the acetone. Additionally present in the stream coming off the ion exchange resin was the unrealized formation of acidic impurities derived from the acidic ion exchange resin. Although not to be held by this theory of the invention, it is believed that acidic ion exchange resins may not be fully polymerized and that held within the network of the solid resin are acidic impurities of an oligomeric nature. When such resins are contacted with appropriate reactants and products, such oligomeric acidic impurities can be leached therefrom and join the product stream. At various points within the downstream processing such acidic impurities may build up to such an extent that they catalyze undesired reactions between the materials present in the stream.

At this point a substantial amount of the bisphenol-A is removed from the stream. Bisphenol-A is unlike other dihydric phenols in that it forms a stable addition adduct with phenol. This physical addition adduct is utilizd in the removal of the bisphenol-A from the stream. Various recovery processes are then utilized to separate the bisphenol-A from the phenol, finally producing a high quality bisphenol-A. The mother liquor from the bisphenol-A phenol adduct has a substantial amount of phenol and a minor amount of bisphenol-A, isomers, IPP, chroman, spiro biindane, and the like.

In order to control the reaction kinetics and provide a balance between the color and side reaction products which can occur in the preparation of bisphenol-A from phenol and acetone, it is important to recycle a substantial portion of a stream having these types of components therein to the reactor which contains the reactants and catalysts system. The quantity of the stream which is recycled depends upon the level of color and side product reactions and impurities which one wishes to maintain or reduce in the actual reaction scheme. This stream can be the actual stream removed as mother liquor from the adduct or it can go through other purification steps which remove quantities of materials which are considered undesirable or which have specific high value and are therefore removed from the process at an early stage. Generally the quantity of material which is recycled to the reactor is from about 85 to about 93 volume percent of the stream. The smaller amount, that is the 7 to about 15 volume percent, is then usually processed to remove the high value contents therefrom. Obviously one of these is bisphenol-A. This was common practice in the hydrochloric acid catalyzed process for preparing bisphenol-A. However, when attempted with an acidic ion exchange resin catalyzed reaction product stream, little or no bisphenol-A was found in the stream where significant quantities were expected.

After a substantial amount of research and testing it was found that there were significant quantities of acidic impurities present in the stream. It appears to be, although we do not wish to limit the invention to this particular theory, these impurities which cause the bisphenol-A to disappear. A postulated mechanism which may account for the disappearance of the bisphenol-A and the appearance of significant color bodies in the recycled material is the acid catalyzed breakdown of bisphenol-A to isopropenylphenol (IPP) and phenol. The former material, IPP, is a highly colored substance.

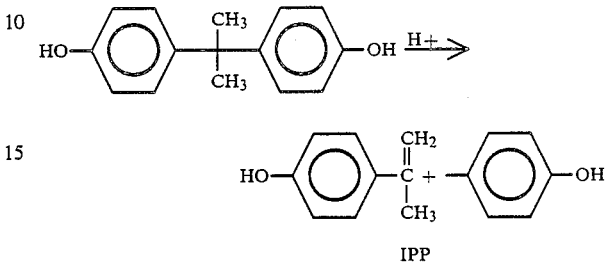

Once more, after substantial research it has now been found that the effects of the acid can be obviated by adding acid neutralizing effective amounts of a carbonate of a Group IIa metal or transition metal of oxidation number +2. Examples of such metals include magnesium, calcium, barium, manganese, cobalt, nickel, copper, zinc and the like. The specific cation surprisingly appears to make a difference in the quality of the stream and quantity of bisphenol-A recovered. It has been found that barium carbonate is the preferred carbonate compound to be added to the processing.

The barium carbonate is added to the minor stream of step (d) which is formed after the major quantity of dihydric phenol has been removed. In processing after the dihydric phenol has been removed from the stream, in particular bisphenol-A as a solid bisphenol-A phenol adduct, the "mother liquor" is then split into two streams, a major and a minor stream. The major stream, as mentioned previously, is recycled to the reaction. The minor stream is then processed for recovery of its constituent materials, including phenol and dihydric phenol. Since it is undesirable for unreacted metal carbonate or metallic products of neutralization to be in contact with the reactor resin, the metal carbonate is added to this minor stream. The removal rocesses for the desirable materials keep the metal products from reaching the reactor resin.

The quantity of metallic carbonate which may be present should be sufficient to recover as much as one would necessarily expect within experimental parameters of bisphenol-A from the minor stream of step (d). This obviously depends upon the quantity of acidic impurities which may be present in the stream and the efficiency of the contact of the metallic carbonate with the acidic impurities in the downstream processing equipment. In present experimentation we have found that from about 0.0025 to about 0.2 weight percent of barium carbonate calculated on the basis of the total stream weight is sufficient to bring about substantial recovery of the bisphenol-A from the minor stream.

Below are examples of the invention. These examples are intended to be illustrative of the scope of the invention and not to limit it therein.

In the examples below, BPA is bisphenol-A, IPP is isopropenyl phenol, 0-P- is the ortho-para isomer of bisphenol-A, "dimer" is PP dimers, BPX-1 is a bisphenol, CR-1 is chroman-1, "spiro" is spirobiindane, BPX-II is a further trisphenol.

In the examples below the following procedures were used. The bisphenol-A was prepared using phenol and acetone and condensing over a sulfonated polystyrene catalyst system. The bisphenol-A phenol adduct was formed and precipitated. The mother liquor was separated from the precipitated adduct. 400 grams of the mother liquor was put into a 1000 ml flask. On the control no additive was added. For the test materials a specific Group II-a or transition metal of oxidation number plus two carbonate was put into a separate 400 gram sample in a certain quantity. Liquid chromatographic analyses were run on the mother liquor starting material to quantify the various amounts of materials present in the mother liquor. A condensor was put into the flask, phenol was condensed from the flask until a temperature of 210° C. was reached. When this temperature was reached, water was put through the condensors to start refluxing. The remainder of the 400 gram sample was refluxed for four hours. After the four hours of refluxing, the material in the flask was then subject to a liquid chromatographic analysis once more. Below are the results of the experiments. All composition values are in grams. % loss refers to % loss in BPA from the starting composition.

|  | START | CONTROL | $ZnCO_3$ 1,000 ppm |
|---|---|---|---|
| Phenol | 338.0 | 49.5 | 39.8 |
| P.P | 42.4 | 22.22 | 40.36 |
| IPP | NDA | .31 | .59 |
| O.P. | 5.15 | 2.48 | 4.56 |
| Dimer | 6.27 | 7.71 | 6.07 |
| BPX-1 | .54 | 1.41 | .59 |
| CR-1 | 3.64 | 2.33 | 3.39 |
| Spiro | .33 | .66 | .34 |
| BPX-II | — | — | — |
| % Loss |  | 47.6% | 4.81% |

|  | START | $MnCO_3$ 1,000 ppm |
|---|---|---|
| Phenol | 340.0 | 33.9 |
| P.P. | 41.6 | 37.1 |
| IPP | NDA | 1.07 |
| O.P. | 5.20 | 4.58 |
| Dimer | 6.1 | 5.84 |
| BPX-1 | .54 | 1.89 |
| CR-1 | 3.52 | 3.47 |
| Spiro | .32 | .36 |
| BPX-II | .58 | .70 |
| % Loss |  | 10.8% |

|  | START | $CaCO_3$ 1,000 ppm |
|---|---|---|
| Phenol | 341.4 | 34.8 |
| P.P. | 33.2 | 25.72 |
| IPP | — | — |
| O.P. | 11.16 | 6.3 |
| Dimer | 4.0 | 4.3 |
| BPX-1 | 2.5 | 2.22 |
| CR-1 | 2.9 | 2.57 |
| Spiro | .112 | .136 |
| BPX-II | 1.23 | 2.70 |
| % Loss |  | 22.53% |

|  | START | CONTROL | $MgCO_3$ 1,000 ppm |
|---|---|---|---|
| Phenol | 338.7 | 49.8 | 30.5 |
| P.P. | 33.9 | 18.6 | 32.4 |
| IPP | NDA | .42 | .75 |
| O.P. | 11.6 | 3.64 | 9.8 |
| Dimer | 4.20 | 4.0 | 4.0 |
| BPX-1 | 2.69 | 1.54 | 1.70 |
| CR-1 | 3.40 | 2.36 | 3.26 |
| Spiro | .10 | .21 | .13 |
| BPX-II | 1.38 | 3.33 | 1.27 |
| % Loss |  | 45.0% | 4.4% |

|  | START | CONTROL | $BaCO_3$ 750 ppm |
|---|---|---|---|
| Phenol | 338.6 | 49.5 | 37.8 |
| P.P. | 42.4 | 22.2 | 41.9 |
| IPP | NDA | .31 | .18 |
| O.P. | 5.15 | 2.48 | 4.75 |
| Dimer | 6.27 | 7.71 | 6.10 |
| BPX-1 | .54 | 1.41 | .50 |
| CR-1 | 3.64 | 2.33 | 3.48 |
| Spiro | .33 | .66 | .35 |
| BPX-II | .63 | 3.21 | .60 |
| % Loss |  | 47.6% | 1.2% |

|  | START | $BaCO_3$ 500 ppm |
|---|---|---|
| Phenol | 341.0 | 35.5 |
| P.P. | 33.44 | 33.3 |
| IPP | — | — |
| O.P. | 11.25 | 10.59 |
| Dimer | 4.03 | 3.93 |
| BPX-1 | 2.60 | 2.40 |
| CR-1 | 3.1 | 3.0 |
| Spiro | .109 | .128 |
| BPX-II | 1.30 | 1.25 |
| % Loss |  | .90% |

|  | START | $BaCO_3$ 1,000 ppm |
|---|---|---|
| Phenol | 340.8 | 37.69 |
| P.P. | 41.5 | 42.12 |
| IPP |  |  |
| O.P. | 4.9 | 4.7 |
| Dimer | 5.8 | 5.8 |
| BPX-1 | .54 | .50 |
| CR-1 | 3.3 | 3.24 |
| Spiro | .314 | .312 |
| BPX-II | .58 | .58 |
| % Loss |  | 0.0% |

|  | START | CONTROL | $BaCO_3$ 1,000 ppm |
|---|---|---|---|
| Phenol | 343.2 | 42.6 | 35.0 |
| P.P. | 32.2 | 21.0 | 32.7 |
| IPP | — | — | — |
| O.P. | 10.8 | 4.2 | 10.6 |
| Dimer | 3.56 | 4.03 | 3.67 |
| BPX-1 | 2.56 | 1.75 | 2.43 |
| CR-1 | 2.66 | 2.01 | 2.68 |
| Spiro | .18 | .25 | .20 |
| BPX-II | 1.12 | 3.23 | 1.16 |
| % Loss |  | 34.7% | 0.0% |

As shown in all examples, the addition of the Group II-a metal or metal of oxidation number +2 $CO_3$ brought about a substantial reduction in lost BPA in comparison to the samples not treated with the metallic carbonate. Barium carbonate was particularly effective.

What is claimed is:
1. A process which comprises
   (a) contacting an excess of a phenol with acetone in the presence of an acidic exchange resin-catalyst;

(b) recovering thereafter a stream, from the acidic ion exchange resin catalyst including bisphenol-A, unreacted phenol, isomers of the desired dihydric phenol and acid impurities derived from the acidic ion exchange resin catalyst;

(c) removing a major portion of bisphenol-A from the stream of (b);

(d) separating the stream including phenol, a small portion of bisphenol-A, isomers of bisphenol-A, and acidic impurities derived from the acidic ion exchange resin catalyst into a major stream and a minor stream by volume;

(e) recycling the major stream so as to contact the acidic ion exchange resin catalyst of (a) together with new phenol and acetone so as to maintain a balance between the color of the final bisphenol-A product and impurities found therein;

(f) recovering from the small stream desirable bisphenol-A and (g) introducing into the minor stream created at step (d) sufficient quantities of a Group II a metal or transition metal of oxidation number +2 carbonate to effectively neutralize the acidic impurities derived from the acidic ion exchange resin catalyst.

2. The process in accordance with claim 1 wherein the cation is selected from the group consisting of magnesium, calcium, barium, manganese, cobalt, nickel, copper and zinc.

3. The process in accordance with claim 2 wherein the cation is zinc, manganese, magnesium, calcium and barium.

4. The process in accordance with claim 3 wherein the cation is barium.

5. In a process for preparing bisphenol-A from the reaction of phenol and acetone in the presence of an acidic ion exchange resin catalyst, the improvement comprising the addition to the process of sufficient quantities of a Group II-a metal or transition metal of oxidation number +2 carbonate to a minor portion of the split process stream created after the removal, from the stream of a major quantity of the bisphenol-A to effectively neutralize acidic impurities provided from the acidic ion exchange resin catalyst, said impurities carried with the bisphenol-A in the downstream processing steps from the catalyst.

6. The process in accordance with claim 5 wherein the cation is selected from the group consisting of magnesium, calcium, barium, manganese, cobalt, nickel, copper and zinc.

7. The process in accordance with claim 6 wherein the cation is zinc, manganese, magnesium, calcium and barium.

8. The process in accordance with claim 7 wherein the cation is barium.

* * * * *

UNITED STATES PATENT AND TRADEMARK OFFICE
CERTIFICATE OF CORRECTION

PATENT NO. : 4,847,433

DATED : July 11, 1989

INVENTOR(S) : Gaylord Michael Kissinger

It is certified that error appears in the above-identified patent and that said Letters Patent is hereby corrected as shown below:

Column 6
Line 68
Add "ion" between "acidic" and "exchange"

Signed and Sealed this

Twenty-first Day of August, 1990

Attest:

HARRY F. MANBECK, JR.

*Attesting Officer*      *Commissioner of Patents and Trademarks*